United States Patent
Viraliur Ponnuswami et al.

(10) Patent No.: US 11,815,426 B2
(45) Date of Patent: Nov. 14, 2023

(54) ROBUST TIRE/WHEEL VIBRATION MONITOR SYSTEM

(71) Applicant: GM GLOBAL TECHNOLOGY OPERATIONS LLC, Detroit, MI (US)

(72) Inventors: Anushya Viraliur Ponnuswami, Markham (CA); Joseph K Moore, Whitby (CA); Halit Zengin, Courtice (CA); Eungkil Lee, Oshawa (CA); Mansoor Alghooneh, Richmond Hill (CA)

(73) Assignee: GM Global Technology Operations LLC, Detroit, MI (US)

(*) Notice: Subject to any disclaimer, the term of this patent is extended or adjusted under 35 U.S.C. 154(b) by 568 days.

(21) Appl. No.: 17/072,486

(22) Filed: Oct. 16, 2020

(65) Prior Publication Data
US 2022/0120638 A1    Apr. 21, 2022

(51) Int. Cl.
*G01M 17/013*    (2006.01)
*B60C 25/00*    (2006.01)
*G07C 5/08*    (2006.01)
*G01M 17/02*    (2006.01)

(52) U.S. Cl.
CPC ......... *G01M 17/013* (2013.01); *B60C 25/007* (2013.01); *G01M 17/025* (2013.01); *G07C 5/0841* (2013.01)

(58) Field of Classification Search
CPC .... G01M 17/013; G01M 17/025; G01M 7/00; B60C 25/007; B60C 23/00; G07C 5/0841; G01H 17/00
See application file for complete search history.

(56) References Cited

U.S. PATENT DOCUMENTS

| | | | | |
|---|---|---|---|---|
| 6,714,858 B2* | 3/2004 | Oblizajek | .............. | B60G 17/00 73/462 |
| 6,865,456 B2* | 3/2005 | Kin | ........................ | B60C 23/061 701/33.9 |
| 2002/0036567 A1* | 3/2002 | Larson | .................. | B60C 23/061 340/444 |

(Continued)

FOREIGN PATENT DOCUMENTS

| CN | 104515687 A | 4/2015 |
|---|---|---|
| DE | 102015000998 A1 | 7/2016 |

(Continued)

*Primary Examiner* — Sizo B Vilakazi
(74) *Attorney, Agent, or Firm* — Quinn IP Law

(57) ABSTRACT

A vibration monitoring system includes a plurality of encoders and an analyzer. The encoders are configured to generate multiple pulse train signals for multiple wheels. Each encoder is coupled to a respective one of the multiple wheels and generates a single one of the pulse train signals. The analyzer is coupled to the encoders and is configured to generate multiple pulse per revolution signals and multiple angular velocity signals for the wheels in response to the pulse train signals. Each pulse per revolution signal conveys a single pulse per rotation of the respective wheel. The analyzer is further configured to generate an input phasor array representative of the pulse per revolution signals, generate a response phasor array in response to the angular velocity signals for the wheels, and generate a report that identifies at least one vibrating wheel in response to the input phasor array and the response phasor array.

20 Claims, 6 Drawing Sheets

(56) References Cited

U.S. PATENT DOCUMENTS

| | | | |
|---|---|---|---|
| 2006/0267750 A1* | 11/2006 | Lu | B60C 23/062 |
| | | | 280/5.502 |
| 2009/0139327 A1* | 6/2009 | Dagh | G01M 1/225 |
| | | | 73/462 |
| 2016/0209291 A1* | 7/2016 | Pita-Gil | G01M 1/28 |
| 2018/0003593 A1 | 1/2018 | Siegel | |

FOREIGN PATENT DOCUMENTS

| | | |
|---|---|---|
| EP | 0902292 A2 | 3/1999 |
| JP | S63138230 A | 6/1988 |

\* cited by examiner

ROBUST TIRE/WHEEL VIBRATION MONITOR SYSTEM

The present disclosure relates to a system and a method for a robust tire/wheel vibration monitor system.

Vibrations are a common occurrence in motor vehicles. The vibrations can arise from internal excitations, such as those caused by irregularities of internal moving parts, including the engine and the wheels. Wheel vibrations are periodic since their pattern recurs for each rotation of the respective wheel. The periodic vibrations exist because of manufacturing variations of the tires and rims, and normal wear of the tires. For example, during tire manufacturing, variations in tire thickness around a tire circumference can create thicker and thinner regions. The irregular thickness can result in a condition referred to as runout, observable through changes in an outside radius of the tire around the circumference. The manufacturing variations can also manifest in localized weight variations as a mass of the tire and rim are unevenly distributed around the tire circumference.

What is desired is an on-vehicle technique for monitoring tire/wheel vibrations.

SUMMARY

A vibration monitoring system is provided herein. The vibration monitoring system includes a plurality of encoders and an analyzer. The plurality of encoders is configured to generate a plurality of pulse train signals for a plurality of wheels. Each of the plurality of encoders is coupled to a respective one of the plurality of wheels and generates a single one of the plurality of pulse train signals. The analyzer is coupled to the plurality of encoders and configured to generate both a plurality of pulse per revolution signals and a plurality of angular velocity signals for the plurality of wheels in response to the plurality of pulse train signals. Each of the plurality of pulse per revolution signals conveys a single pulse per rotation of the respective wheel. The analyzer is further configured to generate an input phasor array representative of the plurality of pulse per revolution signals caused by the plurality of wheels, generate a response phasor array representative of the plurality of angular velocity signals caused by the plurality of wheels, and generate a report that identifies at least one vibrating wheel of the plurality of wheels in response to the input phasor array and the response phasor array.

In one or more embodiments of the vibration monitoring system, the analyzer is further configured to re-initialize in response to a change in a physical condition, the change including at least one or more of a change of tire condition, a tire rotation, a tire replacement, a tire repair, a tire pressure monitoring system sensor replacement, and a fault condition in a corresponding one of the plurality of encoders on at least one of the plurality of wheels.

In one or more embodiments of the vibration monitoring system, the analyzer is further configured with a set of enabling conditions to ensure robust decision making including at least one or more of a tire pressure within a pressure threshold, friction brakes not engaged, a traction control not active, an acceleration within an acceleration threshold, transitional changes due to manufacturing not present, a servicing not present, a prolonged parking not present, and a sensor validity.

In one or more embodiments of the vibration monitoring system, the analyzer is further configured to generate a plurality of matrices for a multiple-input single-output analysis using the input phasor array and the response phasor array.

In one or more embodiments of the vibration monitoring system, the analyzer is further configured to group a plurality of entries of the plurality of matrices into a plurality of low-speed bins and a plurality of high-speed bins.

In one or more embodiments of the vibration monitoring system, the analyzer is further configured to check a plurality of ordinary coherence factors of the plurality of matrices in the plurality of low-speed bins and the plurality of high-speed bins to confirm data sufficiency to perform classification and isolation.

In one or more embodiments of the vibration monitoring system, the analyzer is further configured to generate a plurality of transfer function values in response to the plurality of matrices, and generate a plurality of multiple coherence values in response to the plurality of transfer function values and the plurality of matrices to confirm linearity of the transfer function values.

In one or more embodiments of the vibration monitoring system, the analyzer is further configured to identify the at least one vibrating wheel in response to the plurality of transfer function values in the plurality of low-speed bins and the plurality of high-speed bins.

In one or more embodiments of the vibration monitoring system, the identifying of the at least one vibrating wheel is in response to one or more of historical statistics and an isolation truth table.

A method for wheel vibrational monitoring is provided herein. The method includes generating a plurality of pulse train signals for a plurality of wheels with a plurality of encoders. Each of the plurality of encoders is coupled to a respective one of the plurality of wheels and generates a single one of the plurality of pulse train signals. The method further includes generating both a plurality of pulse per revolution signals and a plurality of angular velocity signals for the plurality of wheels in response to the plurality of pulse train signals with an analyzer. Each of the plurality of pulse per revolution signals conveys a single pulse per rotation of the respective wheel. The method includes generating an input phasor array representative of the plurality of pulse per revolution signals caused by the plurality of wheels, generating a response phasor array representative of a plurality of angular velocity signals caused by the plurality of wheels, and generating a report that identifies at least one vibrating wheel of the plurality of wheels in response to the input phasor array and the response phasor array.

In one or more embodiments, the method further includes re-initializing the analyzer in response to a change in a physical condition, the change including at least one or more of a change of tire condition, a tire rotation, a tire replacement, a tire repair, a tire pressure monitoring system sensor replacement, and a fault condition in a corresponding one of the plurality of encoders on at least one of the plurality of wheels.

In one or more embodiments of the method, a set of enabling conditions to ensure robust decision making in the analyzer includes at least one or more of a tire pressure within a pressure threshold, friction brakes not engaged, a traction control not active, an acceleration within an acceleration threshold, transitional changes due to manufacturing not present, a servicing not present, a prolonged parking not present, and a sensor validity.

In one or more embodiments, the method further includes generating a plurality of matrices for a multiple-input single-output analysis using the input phasor array and the response phasor array.

In one or more embodiments, the method further includes grouping a plurality of entries of the plurality of matrices into a plurality of low-speed bins and a plurality of high-speed bins.

In one or more embodiments, the method further includes checking a plurality of ordinary coherence factors of the plurality of matrices in the plurality of low-speed bins and in the plurality of high-speed bins to confirm data sufficiency to perform classification and isolation.

In one or more embodiments, the method further includes generating a plurality of transfer function values in response to the plurality of matrices, and generating a plurality of multiple coherence values in response to the plurality of transfer function values and the plurality of matrices to confirm linearity of the transfer function values.

In one or more embodiments, the method further includes identifying the at least one vibrating wheel in response to the plurality of transfer function values in the plurality of low-speed bins and the plurality of high-speed bins.

In one or more embodiments of the method, the identifying of the at least one vibrating wheel is in response to one or more of historical statistics and an isolation truth table.

In one or more embodiments of the method, the plurality of wheels support a moving vehicle.

A vehicle is provided herein. The vehicle includes a plurality of wheels, a plurality of encoders and an analyzer. The plurality of wheels is configured to support the vehicle. The plurality of encoders is configured to generate a plurality of pulse train signals for the plurality of wheels. Each of the plurality of encoders is coupled to a respective one of the plurality of wheels and generates a single one of the plurality of pulse train signals. The analyzer is coupled to the plurality of encoders and is configured to generate both a plurality of pulse per revolution signals and a plurality of angular velocity signals for the plurality of wheels in response to the plurality of pulse train signals. Each of the plurality of pulse per revolution signals conveys a single pulse per rotation of the respective wheel. The analyzer is further configured to generate an input phasor array representative of a plurality of pulse per revolution signals caused by the plurality of wheels, generate a response phasor array representative of the plurality of angular velocity signals caused by the plurality of wheels, and generate a report that identifies at least one vibrating wheel of the plurality of wheels in response to the input phasor array and the response phasor array.

The above features and advantages and other features and advantages of the present disclosure are readily apparent from the following detailed description of the best modes for carrying out the disclosure when taken in connection with the accompanying drawings.

DETAILED DESCRIPTION

Embodiments of the disclosure generally provide a vibration analysis methodology and system that detects vibrations in wheel assemblies in each corner of a motor vehicle due to mass imbalances and/or force variations. Both source phasors and response phasors may be constructed from a common encoder signal source. The vibration analysis generally utilizes order tracking, which includes Discrete Fourier Transforms of the encoder signals, extraction of first order phasors, multiple-input multiple-output analysis (or plurality of multiple-input single-output analyses), detection and isolation of suspect corner(s).

A single encoder signal may generate a multiple pulse per revolution signal (e.g., a pulse train signal) at each wheel. Each encoder signal is generally used to construct a pulse per revolution signal (e.g., a single pulse per revolution) for the respective wheels. The methodology and the system may be robust to normal customer use cases (e.g., tire change events, temporary flat spots, and the like) so as to not trigger false error reports. The methodology and the system may also provide isolation logic that is robust against false positives/negatives by incorporating an X-of-Y methodology and hysteresis.

Figure 1:
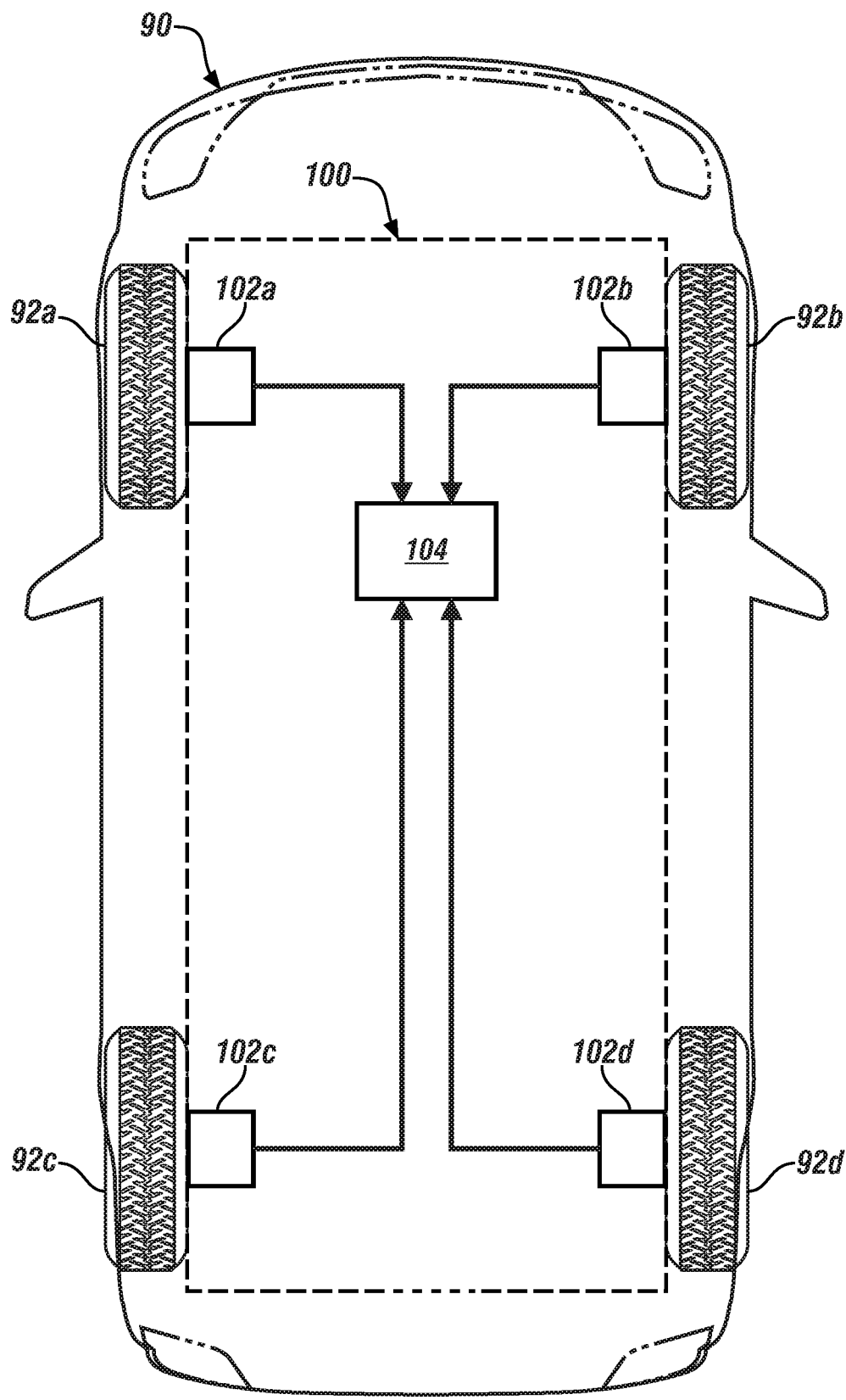
FIG. 1 is a schematic plan diagram illustrating a vehicle.

Referring to FIG. 1, a schematic plan diagram illustrating a vehicle 90 is shown. The vehicle 90 generally comprises multiple wheels 92a-92d and a vibration monitoring system 100. The vibration monitoring system 100 generally comprises multiple encoders 102a-102d and an analyzer 104.

The vehicle 90 may be implemented as an automobile (or car). In various embodiments, the vehicle 90 may include, but is not limited to, a passenger vehicle, a truck, an autonomous vehicle, a gas-powered vehicle, an electric-powered vehicle, a hybrid vehicle, a motorcycle, a single axle trailer and/or a multiple axle trailer. In other embodiments, the vehicle 90 be a device with multiple rotating wheels that travel together on multiple axles, where an on-board detection of a wheel imbalance would be useful. Other types of vehicles 90 may be implemented to meet the design criteria of a particular application.

The wheels 92a-92d may implement road wheels. The wheels 92a-92d are generally operational to provide for support and movement of the vehicle 90 across the ground. In various embodiments, each wheel 92a-92d may include a tire mounted on a rim. The wheels 92a-92d may be used to provide traction between the vehicle 90 and the ground upon which the vehicle 90 is sitting.

The vibration monitoring system 100 may use the on-board corner wheel speed encoders 102a-102d to generate the pulse train signals. The on-board analyzer 104 may construct the pulse per revolution signals from the pulse train signals. The analyzer 104 may also construct an angular velocity signal for each of the wheels 92a-92d from the pulse train signals. The pulse per revolution signals may be used to extract tire first order phasors of the source signals. The pulse train signals may also be used as the response signals. The analyzer 104 and the encoders 102a-102d generally eliminate externally mounted instrumentation and/or additional hardware attached to the vehicle 90 to monitor the wheel vibrations and identify a vibrating wheel 92a-92d.

The analyzer 104 may perform an order tracking of the encoder signals using a multiple-input multiple-output analysis or a plurality of multiple-input single-output analyses at defined quasi-static speed ranges, including at lower speed ranges and higher speed ranges. In various embodiments, the multiple-input multiple-output analysis may be implemented. In other embodiments, the multiple-input single-output analyses may be implemented. The order tracking method may have a reduced number of inverse operations in the multiple-input multiple-output analysis. The order tracking method may utilize pre-initialized twiddle factors for faster execution of the Discrete Fourier Transforms.

The vibration monitoring system 100 is designed with a set of enabling conditions to ensure robustness of the decision making. The enabling criterion may include tire pressures within a calibrated upper threshold and lower threshold of a nominal tire pressure as changes in tire pressure may lead to changes in tire stiffness, which may lead to changes in the resonant frequency of the unsprung mass. Another enabling criterion may include friction brakes not being engaged to ensure that a brake pulsation vibration does not contribute to the tire wheel vibration analysis. Another enabling criterion may include a traction control system of the vehicle 90 not being active as the traction control system may apply additional external torques to one or more wheels. Another enabling criterion may include a vehicle speed within a calibrated threshold as the effect of tire vibration may be pronounced within a specific speed range. Another enabling criterion may include vehicle longitudinal acceleration within calibrated thresholds as changes to acceleration may impact the steady state evaluation of the system. Another criteria may include disabling the vibration monitoring system 100 for the first few hundred kilometers of vehicle ownership to remove temporary variations and flat spots that may have been created due to manufacturing processes. Additional criteria may include disabling the vibration monitoring system 100 if the vehicle 90 has been stationary for a time greater than a calibrated threshold, or when changes to a tire/wheel assembly have been made. The vibration monitoring system 100 may be re-enabled when the vehicle 90 has been driven above a calibrated speed for a calibrated time. This criteria may ensure that the vibration monitoring system 100 does not trigger false positives due to temporary flat spots caused by prolonged parking or service processes. Additional enabling criteria may include validity for tire pressure monitoring system signals, friction brake pressure signals, a vehicle speed signal, a longitudinal acceleration signal, and a vehicle odometer signal received on the communication network to ensure the vibration monitoring system 100 is robust to system faults.

The vibration monitoring system 100 is generally designed to have an intelligent reinitialization feature that automatically detects specific use cases, like changes to the tire/wheel system, and triggers a reinitialization of the data (in addition to a first initialization of the vehicle 90). The vibration monitoring system 100 may use a pressure signal generated by a tire pressure monitoring system to detect if a deflation event has occurred and then reinitialize the system (e.g., restarting if there is change to a tire, a wheel rim, or repair to a tire). An auto-location feature of the tire pressure monitoring system may also be used to detect if a new tire pressure monitoring system sensor installation and/or tire rotation has occurred, and subsequently reinitialize the system. The vibration monitoring system 100 may also detect if there is a fault among the encoders 102a-102d and execute the reinitialization. Finally, a manual system reinitialization may be performed should a service personnel or an operator wish to reinitialize the vibration monitoring system 100. The reinitializations may be done to ensure that the vibration monitoring system 100 provides an accurate assessment of a current physical condition.

The encoders 102a-102d may implement wheel speed sensors. Each encoder 102a-102d may be connected to and rotate with a respective one of the wheels 92a-92d. The encoders 102a-102d are generally operational to generate the pulse train signals. Each pulse train signal may convey a sequence of pulses. Multiple pulses may be generated for each rotation of the respective wheel 92a-92d. For example, each encoder 102a-102d may generate an integer number of pulses (e.g., N) for each rotation of the respective wheel 92a-92d. A frequency of the pulses is generally based on a rotational speed of the respective wheel 92a-92d.

The analyzer 104 may implement one or more microcontrollers. The analyzer 104 is generally operational to generate the multiple pulse per revolution signals and the multiple angular velocity signals for the wheels 92a-92d in response to the pulse train signals. A pulse per revolution signal may be generated for each respective wheel 92a-92d. Each pulse per revolution signal may convey a single pulse per rotation of the respective wheel 92a-92d. The analyzer 104 may also be operational to generate an input (source) phasor array representative of multiple pulse per revolution signals caused by the wheels 92a-92d, and generate a response phasor array representative of the angular velocity signals caused by the wheels 92a-92d. The analyzer 104 may be further operational to generate a report that identifies at least one vibrating wheel of the wheels 92a-92d in response to the input phasor array and the response phasor array used in the multiple-input multiple-output analysis or the plurality of multiple-input single-output analyses.

Each microcontroller may include one or more processors, each of which may be embodied as a separate processor, an application specific integrated circuit (ASIC), a field programmable gate array (FPGA), or a dedicated electronic control unit. The microcontrollers may include tangible, non-transitory memory, (e.g., read-only memory, nonvolatile memory, and/or flash memory). Accompanying hardware in the form of a high-speed clock or timer, analog-to-digital and digital-to-analog circuitry, and input/output circuitry and devices, as well as appropriate signal conditioning and buffer circuitry may be implemented in the microcontrollers.

Computer-readable and executable instructions embodying the present disclosure may be stored in the memory and executed as set forth herein. The executable instructions may be a series of instructions employed to run applications on the microcontrollers. The microcontrollers may receive commands and information, in the form of one or more input signals from various controls and/or components in the vehicle 90, and communicate instructions to a user (or driver) display and/or an electrical diagnostics port through one or more control signals.

Figures 2, 3:
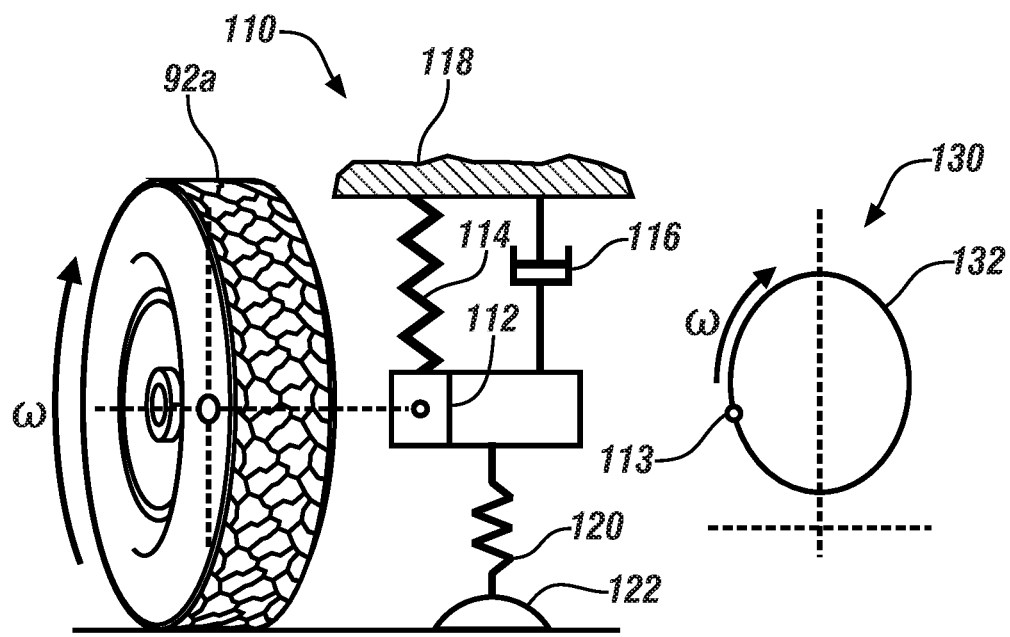
FIG. 2 is a schematic perspective diagram of a simplified quarter-car model for a wheel of the vehicle in accordance with an exemplary embodiment.
FIG. 3 is a schematic diagram of a model of an unbalanced mass in accordance with an exemplary embodiment.

Referring to FIG. 2, a schematic perspective diagram of an example simplified quarter car model 110 of a wheel 92a is shown in accordance with an exemplary embodiment. The wheel 92a may be modeled as a mass 112 connected by a spring 114 and a damper 116 in parallel to a reference (e.g., a floating mass) 118. The mass 112 may also be connected by a smaller spring 120 that represents a tire compliance from the mass 112 to the ground 122. The wheel 92a may have a rotational speed w. While the wheel 92a is balanced, the rotation of the wheel 92a may be modeled by the mass 112 remaining stationary relative to the reference 118. While the wheel 92a is unbalanced, the rotation of the wheel 92a may be modeled by an unbalanced mass 113 (see FIG. 3) rotating relative to the reference 118.

Referring to FIG. 3, a schematic diagram of an example model 130 of the unbalanced mass 113 is shown in accordance with an exemplary embodiment. The x-axis of the model 130 may represent a horizontal motion of the unbalanced mass 113. The y-axis of the model 130 may represent a vertical motion of the unbalanced mass 113. The unbalanced mass 113 may move along an orbit 132 at the rotational speed w.

Figure 4:
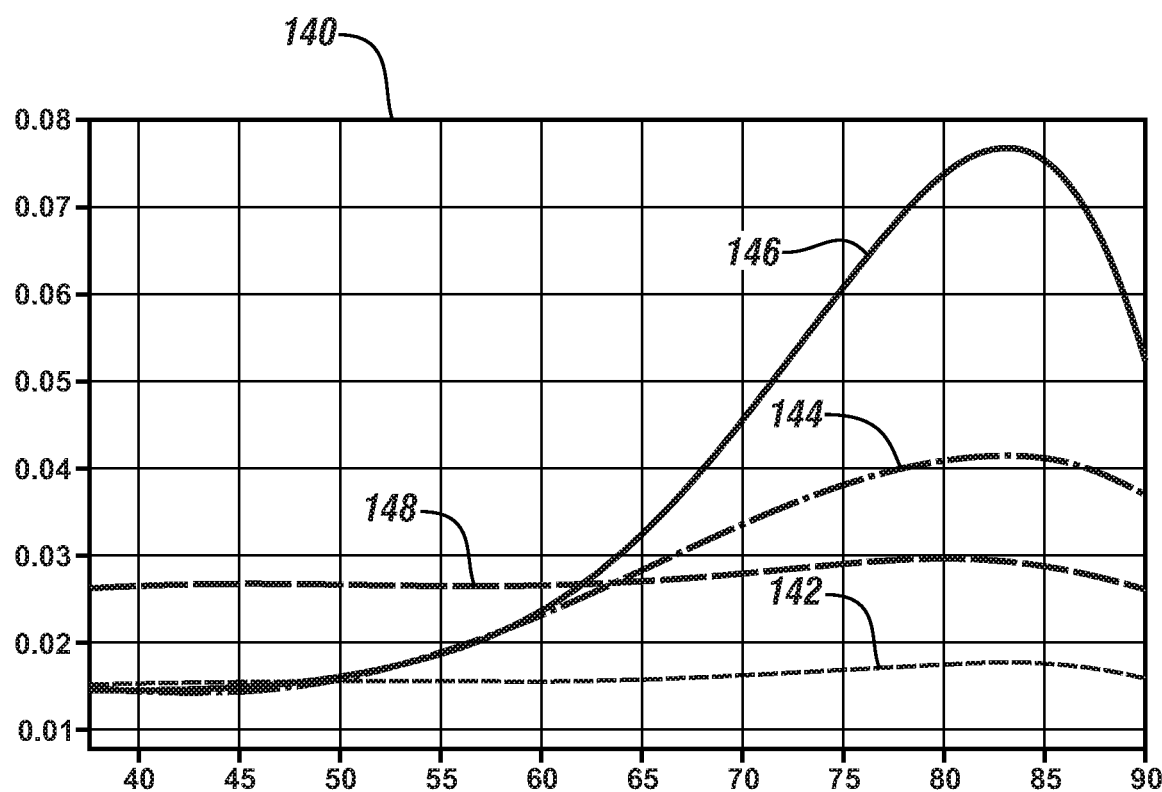
FIG. 4 is a graph of transfer functions of the wheel in accordance with an exemplary embodiment.

Referring to FIG. 4, a graph 140 of example transfer function magnitudes of the wheel 92a is shown in accordance with an exemplary embodiment. The x-axis of the graph 140 may represent a speed of the vehicle 90 in units of miles per hour. The y-axis of the graph 140 may represent a transfer function magnitude of the wheel 92a relative to the vehicle 90 in units of rotations per second$\times 10^2$.

A curve 142 shows the transfer function magnitude of the wheel 92a while the wheel 92a is balanced. A curve 144 generally shows the transfer function magnitude of the wheel 92a while the wheel 92a is slightly unbalanced (e.g., a 2-ounce mass imbalance). A curve 146 may illustrate the transfer function magnitude of the wheel 92a while the wheel 92a is modestly unbalanced (e.g., a 4-ounce mass imbalance). A curve 148 may show the transfer function magnitude of the wheel 92a with a force variation (e.g., 20 pounds). The unbalanced masses in the example curves 144, 146 and 148 generally show a peak transfer (e.g., vibration) of the wheel 92a around 82 miles per hour. Other peak speeds and transfer function magnitudes may be realized with different suspension configurations based on different masses, stiffnesses, and damping and/or different mass imbalances.

Figure 5:
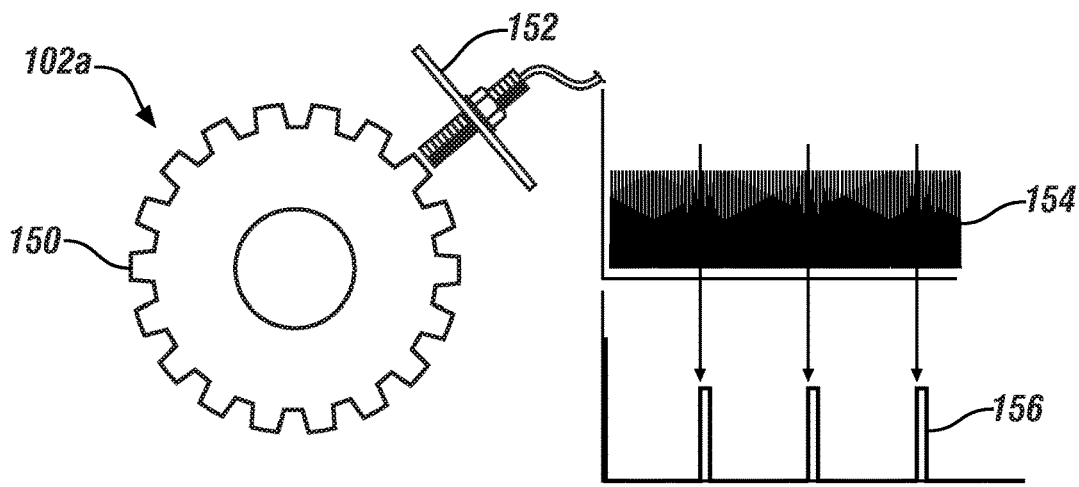
FIG. 5 is a schematic side view diagram of an implementation of an encoder in accordance with an exemplary embodiment.

Referring to FIG. 5, a schematic side view diagram of an example implementation of the encoder 102a is shown in accordance with an exemplary embodiment. The encoder 102a generally comprises a tone wheel 150 and a sensor 152.

The tone wheel 150 may be referred to as a tone ring or a reluctor. The tone wheel 150 may have multiple (e.g., N) teeth (or a multitude of N-S poles) spaced around a perimeter of the wheel. A single tone wheel 150 may be connected to a rotating axis of each wheel 92a-92d. As the respective wheel 92a-92d rotates, the teeth/poles of the tone wheel 150 may move past the sensor 152.

The sensor 152 may implement a magnetic sensor. A single sensor 152 may be connected to a structure of the suspension proximate a respective tone wheel 150. In various embodiments, the sensor 152 may be a reluctance sensor or a magneto-resistive sensor. The sensor 152 is generally operational to generate the respective pulse train signal 154 in response to the teeth of the tone wheel 150 moving past the sensor 152.

As the tone wheel 150 rotates, the sensor 152 may detect a change in separation between teeth/poles of the tone wheel 150 and a free end of the sensor 152. The sensor may generate the pulse train signal 154 in response to the motion of the teeth/poles of the tone wheel 150. The pulse train signal 154 may convey a single pulse as each tooth/pole of the tone wheel 150 passes by the sensor 152. The N teeth/poles of the tone wheel 150 may result in N pulses in the pulse train signal 154 per wheel rotation during a sample time.

The pulse train signal 154 from each encoder 102a-102d may be conveyed to the analyzer 104. The analyzer 104 may convert each pulse train signal 154 into a pulse per revolution signal 156. Each pulse per revolution signal 156 may have a single pulse for each revolution of the respective wheel 92a-92d.

Figure 6:
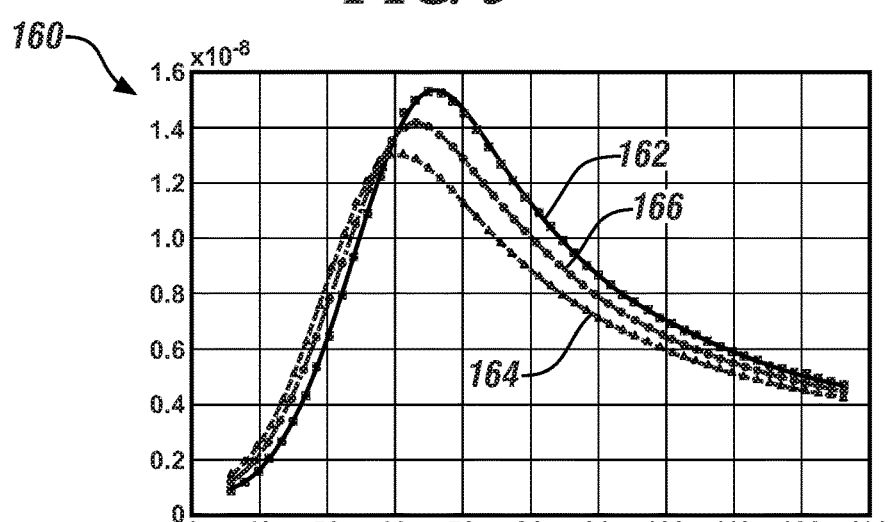
FIG. 6 is a graph of a power spectral density of the wheel as a function of tire stiffness in accordance with an exemplary embodiment.

Referring to FIG. 6, a graph 160 of an example power spectral density of a wheel as a function of tire stiffness is shown in accordance with an exemplary embodiment for a given unbalanced mass 113. The x-axis of the graph 160 may represent a speed of the vehicle 90 in units of kilometers per hour. The y-axis of the graph 160 may represent a power spectral density of wheel displacement (e.g., 92a) relative to the vehicle 90 in units of meters.

A curve 166 generally shows the transfer function magnitude of the wheel 92a having a baseline stiffness (or tire pressure). A curve 162 may show the transfer function magnitude of the wheel 92a at a higher stiffness (e.g., +10% tire stiffness). A curve 164 may show the transfer function magnitude of the wheel 92a at a lower stiffness (e.g., −10% tire stiffness). Each curve 162-166 generally illustrates the effect that the wheel 92a imparts into a frame of the vehicle 90 as a function of frequency. Changes in the tire stiffness generally change a resonant frequency and a resonance amplitude of an unsprung mass. The unsprung mass may be a mass of the wheel, the suspension and other directly connected components.

Figure 7:
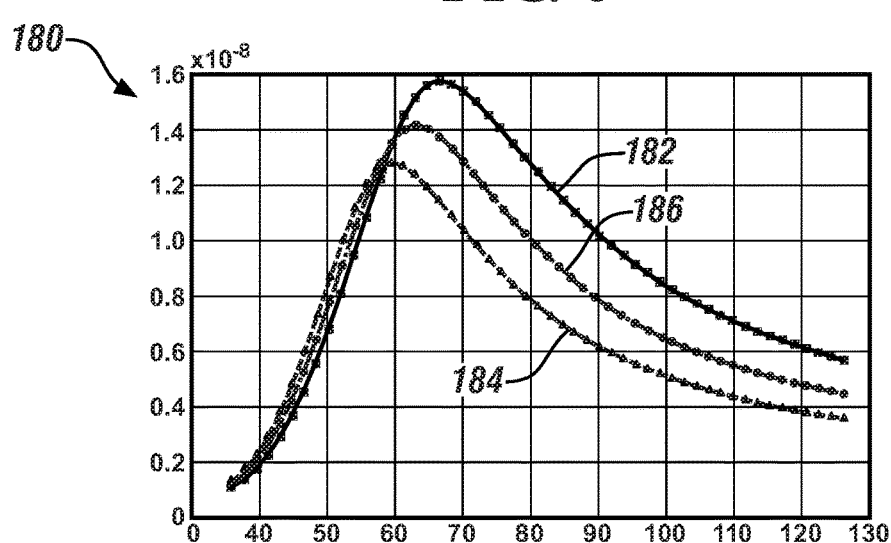
FIG. 7 is a graph of a power spectral density of the wheel as a function of unsprung mass in accordance with an exemplary embodiment.

Referring to FIG. 7, a graph 180 of an example power spectral density of a wheel as a function of the unsprung mass is shown in accordance with an exemplary embodiment for a given unbalanced mass 113. The x-axis of the graph 180 may represent a speed of the vehicle 90 in units of kilometers per hour. The y-axis of the graph 180 may represent a power spectral density of wheel displacement (e.g., 92a) relative to the vehicle 90 in units of meters.

A curve 186 generally shows the transfer function magnitude of a baseline unsprung mass. A curve 182 may show the transfer function magnitude of a lower unsprung mass (e.g., −10% unsprung mass). A curve 184 may show the transfer function magnitude of a higher unsprung mass (e.g., +10% unsprung mass). Each curve 182-186 generally illustrates the power that the unsprung mass imparts into the frame of the vehicle 90 as a function of frequency. Changes in the unsprung mass generally change a resonant frequency and a resonance amplitude of the unsprung mass.

The vibration analysis methodology generally has multiple calibratable bins (e.g., several low-speed bins and several high-speed bins) to accommodate changes to the unsprung mass and the tire stiffness. The vibration analysis methodology may also isolate the suspect corner by accounting for a history of the decisions to make a statistically confident conclusion of the suspect corner(s) causing the vibration.

Figure 8:
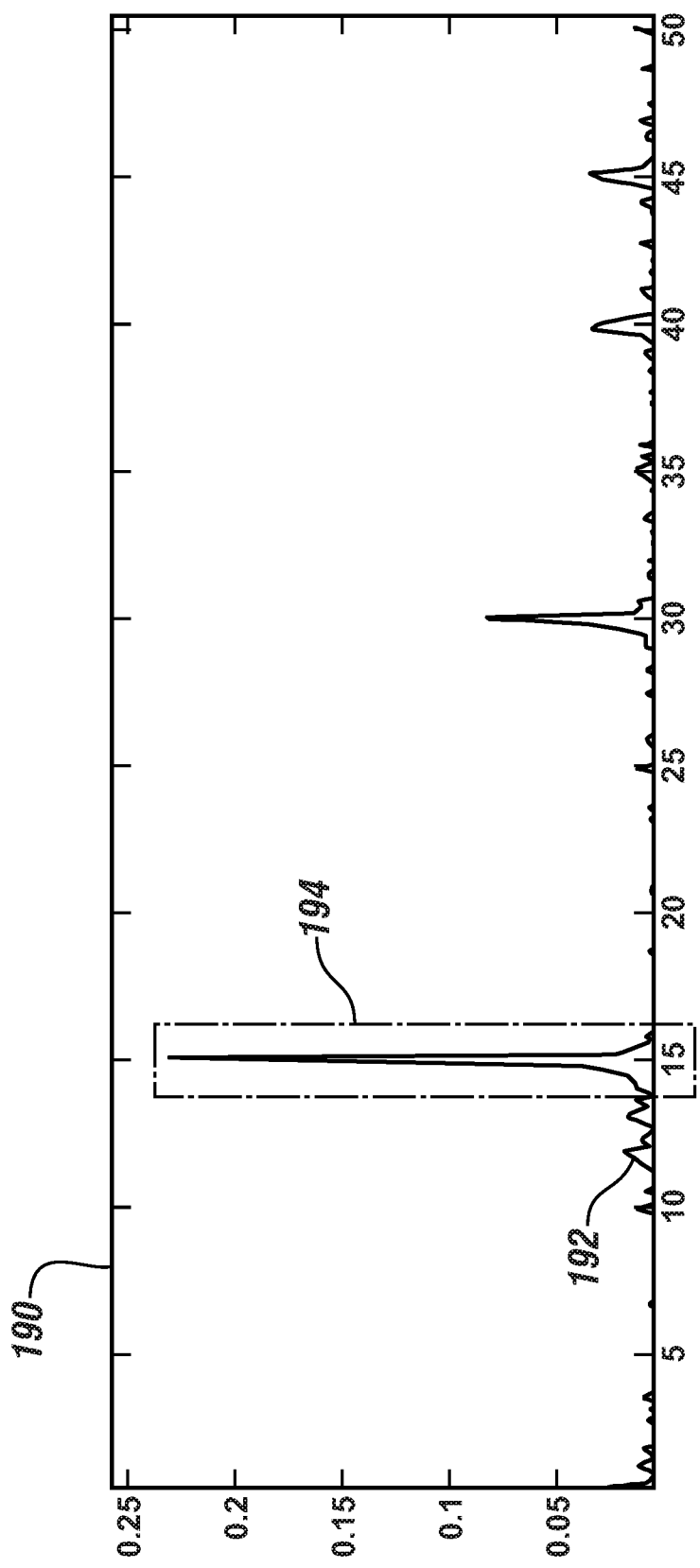
FIG. 8 is a graph of a Discrete Fourier Transform of angular velocity signals exhibiting different wheel orders in accordance with an exemplary embodiment.

Referring to FIG. 8, a graph 190 of an example Discrete Fourier Transform of the angular velocity signals exhibiting different wheel orders is shown in accordance with an exemplary embodiment. The x-axis of the graph 190 may represent the vibration frequency in hertz. The y-axis of the graph 190 may represent an amplitude of the wheel 92a relative to the vehicle 90 in units of rotations per second× $10^2$.

A curve 192 generally illustrates the vibration of the wheel 92a. The tire rotational frequency (e.g., 15 hertz in the example) may be calculated by the analyzer 104 from the pulse per revolution signal 156. A first order phasor content 194 corresponding to the frequency may be extracted for both the pulse per revolution signal 156 and the response angular velocity signal. The first order phasor content 194 of both the pulse per revolution signal 156 and the angular velocity signal may be used in the analysis.

Figure 9:
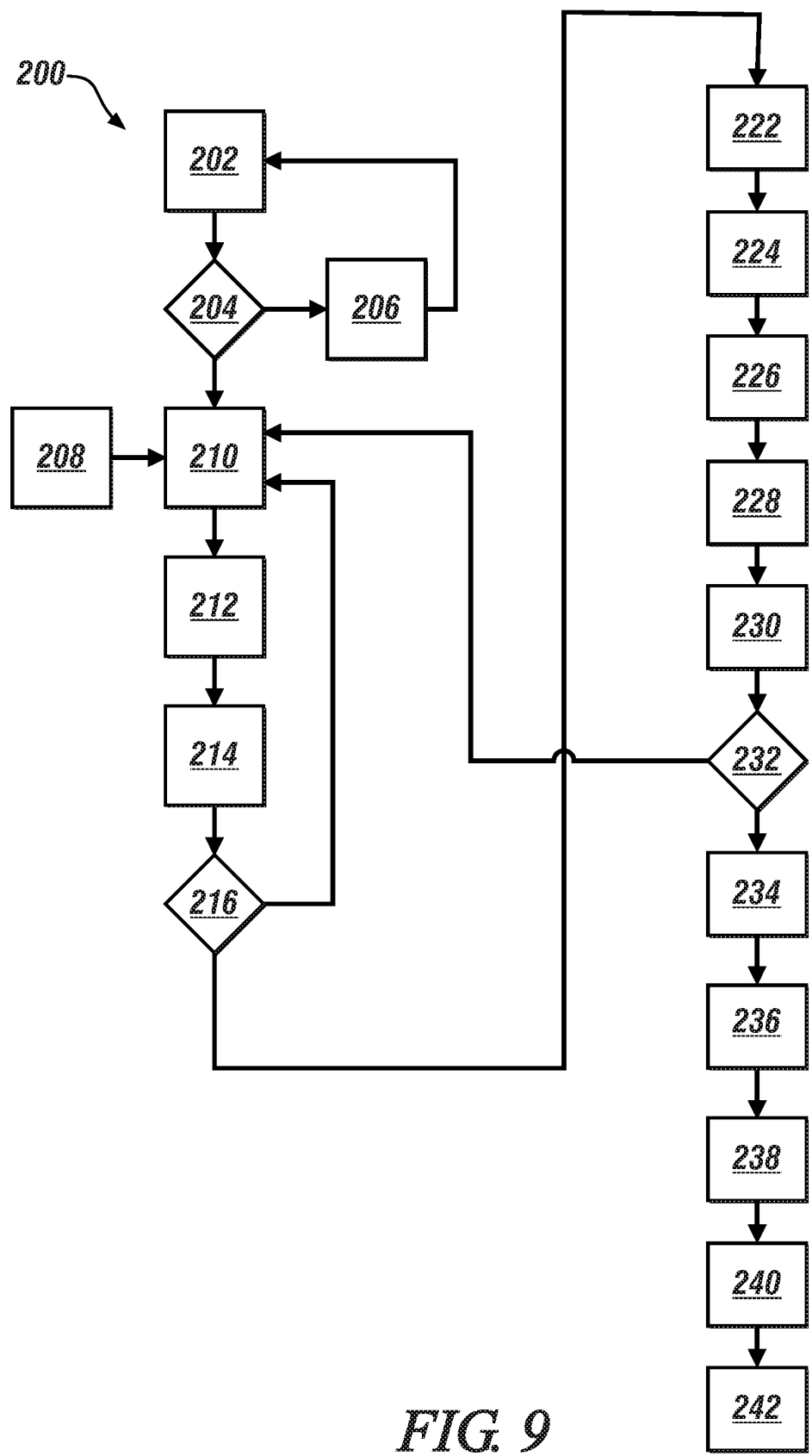
FIG. 9 is a flow diagram of a vibration detection method in accordance with an exemplary embodiment.

Referring to FIG. 9, a flow diagram of an example vibration detection method 200 is shown in accordance with an exemplary embodiment. The method (or process) 200 may be implemented by the vibration monitoring system 100. The method 200 generally comprises a step 202, a step 204, a step 206, a step 208, a step 210, a step 212, a step 214, a step 216, a step 222, a step 224, a step 226, a step 228, a step 230, a step 232, a step 234, a step 236, a step 238, a step 240, and a step 242. The sequence of steps is shown as a representative example. Other step orders may be implemented to meet the criteria of a particular application.

The vibration detection may start in the step 202. In the step 204, the analyzer 104 may check for a reset event triggered as a result of either a tire deflation event (change to a tire, a wheel rim or repair to a tire), a new tire pressure monitoring system sensor, a tire rotation, a manual system reset, or an improperly functioning (or questionable) encoder 102a-102d. If one or more of the aforementioned events occur, data from the analyzer 104 may be erased in the step 206 and the method 200 returns to the step 202.

If the encoders 102a-102d are operating correctly, the encoders 102a-102d may generate and present the pulse train signals 154 to the analyzer 104 in the step 208. The analyzer 104 may timestamp the pulse train signals 154 in the step 208. The analyzer 104 then generates a pulse per revolution signal 156 and an angular velocity signal for each wheel 92a-92d from the pulse train signals 154 and the time stamps in the step 210.

In the step 212, the analyzer 104 may buffer multiple (e.g., 128, 256, 512 or 1024) samples of the angular velocity signals and the pulse per revolution signals 156. Enabling conditions may be assessed by the analyzer 104 in the step 214. The enabling conditions may include the following: tire pressures of vehicle 90 are within a calibrated upper and lower threshold; friction brakes of vehicle 90 are not engaged; the traction control system of vehicle 90 is not active; the speed of vehicle 90 is within a calibrated upper and lower threshold; an acceleration of vehicle 90 is within a calibrated upper and lower threshold; an odometer of vehicle 90 is more than a calibrated threshold; the speed of vehicle 90 has exceeded a calibrated threshold for a calibrated time following a period where the vehicle has been stationary for a time greater than a calibrated threshold or after changes to a tire/wheel assembly of vehicle 90; a validity of tire pressure monitoring signals, friction brake pressure signals, a vehicle speed signal, an acceleration signal, and a vehicle odometer signal of vehicle 90. If one or more of the enabling conditions are not meet per the step 216, the method 200 may return to the step 210. If the enabling conditions are met per the step 216, the method 200 may continue with the step 222.

The buffered data may be transformed into the frequency domain and phasor quantities of first order content are extracted. In the step 222, the analyzer 104 may calculate the Discrete Fourier Transforms of the angular velocity signals and the pulse per revolution signals 156 using a Hanning Window and a 50% overlap criteria. For example, a first record may be taken from 0 to 2.56 seconds, a second record from 1.28 to 3.84 seconds, and a third record from 2.56 to 5.12 seconds. The analyzer 104 may extract first order phasors from the Discrete Fourier Transforms in the step 224.

The first order phasors may be extracted to include 'n' points from each pulse per revolution signal 156 and angular velocity signal. The points may be selected such that a peak frequency is included. Based on selected 'n' points, an input phasor array X and the response phasor array Y for the corresponding corner assembly are generally created per equation 1 as follows:

$$X_i = \begin{bmatrix} X_{1i} \\ X_{2i} \\ \vdots \\ X_{ni} \end{bmatrix} Y_i = \begin{bmatrix} y_{1i} \\ y_{2i} \\ \vdots \\ y_{ni} \end{bmatrix} i = 1, 2, \ldots, p \qquad \text{Eq. (1)}$$

Where 'p' represents the number of tire/wheel assemblies.

To facilitate the calculations, the input phasor quantities $X_i'$ are normalized to unity magnitude per equation 2 as follows:

$$\overline{X}_i = \frac{1}{\sqrt{x_i^* x_i}} X_i \qquad \text{Eq. (2)}$$

Where (·)* represents complex conjugate transpose or Hermitian transpose.

The input phasors $\overline{X}_i$ and the response phasors $Y_i$ may be concatenated per equations 3 and 4 as follows:

$$X = [\overline{X}_1 \overline{X}_2 \ldots \overline{X}_p] \qquad \text{Eq. (3)}$$

$$Y = [Y_1 Y_2 \ldots Y_p] \qquad \text{Eq. (4)}$$

The input phasor array X may be n×p with complex entries that organizes the input phasor quantities of the pulse per revolution signals 156. The response phasor array Y is generally n×p with complex entries that organizes the response phasor quantities of the angular velocity signals.

The analyzer 104 generally records the count records in the time domain and then converts the count records into the frequency domain corresponding to the rotation of the wheels 92a-92d. Accordingly, each entry of the input phasor array X of equation 3 is in the format of $Ae^{i\varnothing}$ as a phasor quantity. Here, e is the exponential number, i is an imaginary number (sqrt (−1)) and Ø is the angular position with respect to the wheel rotation.

The analyzer 104 may generate the data points of $Y_1 \ldots Y_P$ in equation 4. The data points $Y_1 \ldots Y_P$ may be transformed into the frequency domain and transformed into phasor quantities in the format of $Ae^{i\varnothing}$. The rows of the response phasor array Y generally represent the individual time records corresponding to the rows of the input phasor array X. Accordingly, each entry of the response phasor array Y of equation 4 is in the format of $Ae^{i\varnothing}$ as a phasor quantity. Here, e is the exponential number, i is an imaginary number (sqrt (−1)) and Ø is the phase of the resulting vibration in at least one of the wheels 92a-92d.

The X and Y phasor arrays are generally utilized to recursively update auto correlation and cross correlation matrices $S_{XX}$, $S_{XY}$, and $S_{YY}$ for a multiple-input multiple-output analysis in the step 226 using equations 5, 6 and 7 as follows:

$$S_{XX} = S_{\overline{XX}} + X^*X \qquad \text{Eq. (5)}$$

$$S_{XY} = S_{\overline{XY}} + X^*Y \qquad \text{Eq. (6)}$$

$$S_{YY} = S_{\overline{YY}} + Y^*Y \qquad \text{Eq. (7)}$$

Where $(\cdot)^-$ represents the previous calculated matrix.

In the step 228, the S-matrices entries may be grouped into respective speed bins by the analyzer 104. To increase the accuracy of the generated phasors, the vehicle 90 is generally driven long enough so that the wheels 92a-92d are phased out with respect to each other. This ensures that the $S_{XX}$ matrix is far from singular and the wheel pulse per revolution signals 156 are distinguishable. A metric to determine this is an ordinary coherence (or data sufficiency criteria), which is a ratio of the cross correlation of the input signals to the auto correlation. The coherence of the cross-component values may be calculated per equation 8 as follows:

$$\gamma_{ij}^2 = \frac{S_{XX}(i,j)^* S_{XX}(i,j)}{S_{XX}(i,j) S_{XX}(i,j)}, i \neq j \qquad \text{Eq. (8)}$$

A check for ordinary coherence may be performed in the step 230. The ordinary coherence array is a p×p symmetric array with each element representing the correlation of the plurality of pulse per revolution signals with each pair of tire wheel assemblies and themselves. The ordinary coherence values $\gamma_{ij}^2$ may be compared to a first threshold value (e.g., 0.3) in the step 232. If one or more of the coherence values $\gamma_{ij}^2$ are greater than the first threshold value, the method 200 may return to the step 210. If each of the coherence values $\gamma_{ij}^2$ are less than or equal to the first threshold value, the method 200 may continue with the step 234.

In the step 234, the analyzer 104 may calculate a transfer function H per equation 9, where each element of the leading diagonal represents the transfer function phasor for a corresponding corner whose magnitude is represented by |H|.

$$H = S_{XX}^{-1} S_{XY} \qquad \text{Eq. (9)}$$

A criterion to ensure linearity of the system is calculated in step 234. It is understood as multiple coherence (linearity criteria) which ensures that the system is linear. The multiple coherence may have value between 0 and 1. A value of 1 generally indicates that the inputs in the series are linearly related to the output, while a value of 0 may indicate that none of the inputs are correlated to the output. The multiple coherence is a p×p array whose leading diagonal elements indicate what level of vibration at a particular corner is attributed to the corresponding corner assembly. The multiple coherence may be calculated by equation 10 as follows:

$$\Gamma = H^* S_{XY} S_{YY}^{-1} \qquad \text{Eq. (10)}$$

The magnitudes of the elements of the leading diagonal of multiple coherence value $\Gamma_{ii}$ may be compared to a second threshold value (e.g., 0.7) in the step 236. For each of the values $\Gamma_{ii}$ less than the second threshold, the corresponding transfer function magnitudes are set to Not Available in step 236 and the method 200 may continue with step 238.

In the step 238, the high-speed transfer function magnitudes and the low-speed transfer function magnitudes may be assigned to the enabled bins of a calibrated speed bin array by the analyzer 104. The bins are generally selected such that the low-speed bins correspond to the linear range of operation and the high-speed bins correspond to the resonance speed of the unsprung mass of the vehicle 90. The analyzer 104 may use the values in the enabled bins to isolate a vibrating wheel 92a-92d in the step 240. When a vibrating wheel 92a-92d (e.g., a wheel with excessive and consistent vibrations) is found, the analyzer 104 may generate a report in the step 242. The report may be in the form of an indication to a driver of the vehicle 90 and/or an electronic record readable through a diagnostic port of the vehicle 90.

Figure 10:
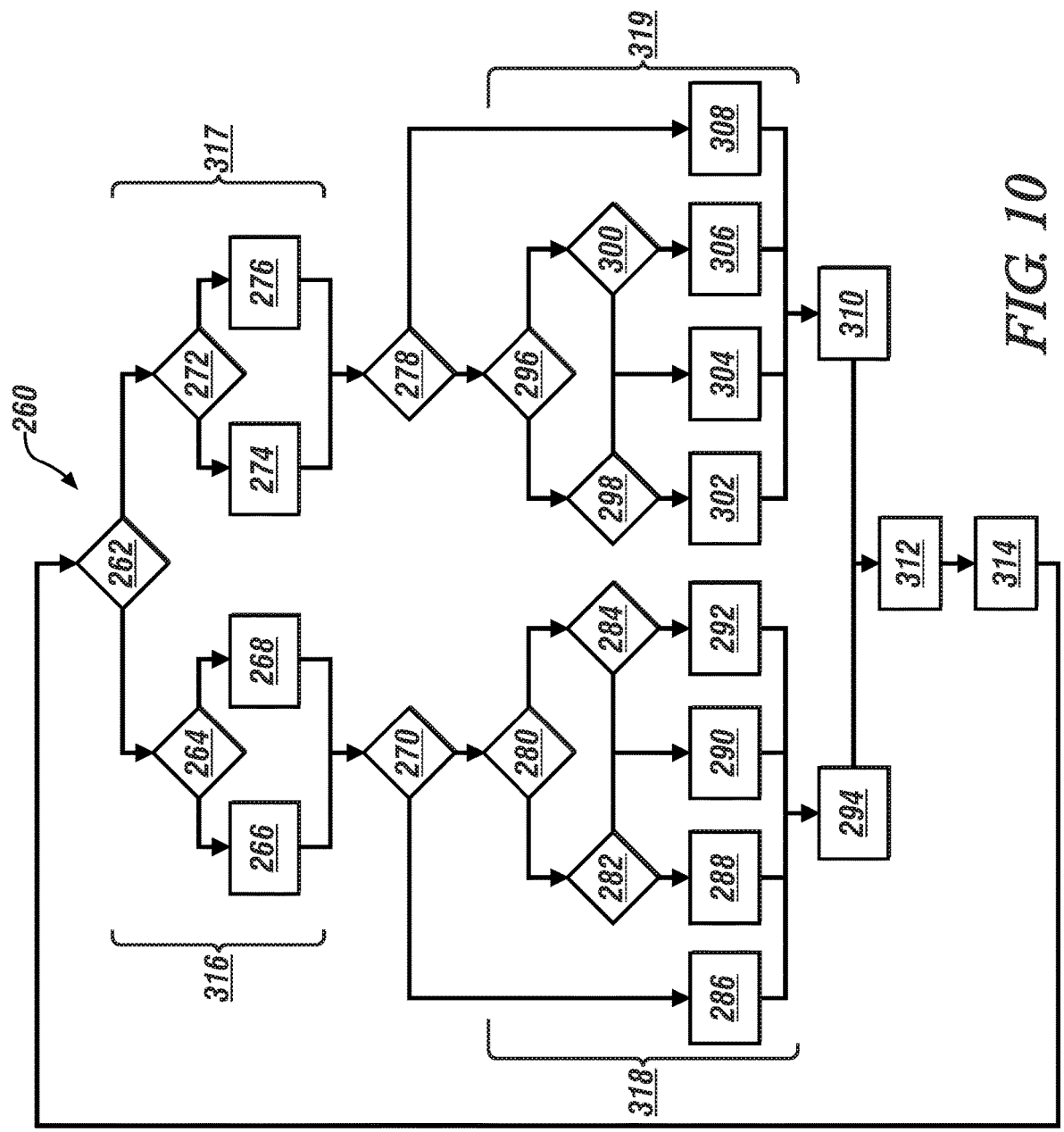
FIG. 10 is a flow diagram of an isolation method in accordance with an exemplary embodiment.

Referring to FIG. 10, a flow diagram of an example isolation method 260 is shown in accordance with an exemplary embodiment. The method (or process) 260 may be implemented by the vibration monitoring system 100. The method 260 may implement the step 240 shown in FIG. 9. The method 260 generally comprises a step 262, a step 264, a step 266, a step 268, a step 270, a step 272, a step 274, a step 276, a step 278, a step 280, a step 282, a step 284, a step 286, a step 288, a step 290, a step 292, a step 294, a step 296, a step 298, a step 300, a step 302, a step 304, a step 306, a step 308, a step 310, a step 312, a step 314, an assessment 316, an assessment 317, an assessment 318, and an assessment 319. The sequence of steps is shown as a representative example. Other step orders may be implemented to meet the criteria of a particular application. The method 260 generally provides for classification and/or isolation of vibrating wheels 92a-92d. The classification may indicate where a vibrating wheel exceeds a threshold or not. Results of the classification may include a true condition, a false condition, and a not available condition.

In the step 262, the speed range of transfer function magnitude |H| may be considered by the analyzer 104. If the speed range of a particular |H| is considered a high-speed value, then the variable $H_{HS}$ is assigned the value of the transfer function magnitude |H| according to equation 11 and the method may continue with the step 264.

$$H_{HS} = |H| \qquad \text{Eq. (11)}$$

If the speed range of a particular |H| is considered a low-speed value, then the variable $H_{LS}$ is assigned the value of the transfer function magnitude |H| according to equation 12 and the method may continue with the step 272.

$$H_{LS} = |H| \qquad \text{Eq. (12)}$$

The individual high-speed values $H_{HS}$ may be individually assessed in assessment 316 in the steps 264, 266, and 268. An individual high-speed value $H_{HS}$ may be compared to a high-speed threshold (e.g., $HS_{th}$) in the step 264. If the high-speed value $H_{HS}$ is less than or equal to the high-speed threshold $HS_{th}$, the high-speed value $H_{HS}$ may be marked as a low value in the step 266. If the high-speed value $H_{HS}$ is greater than the high-speed threshold $HS_{th}$, the high-speed value $H_{HS}$ may be marked as a high value in the step 268.

In the step 270, a check may be made to determine if several (e.g., L) $H_{HS}$ data items have filled the high-speed bin array. If not, the method 260 may continue with step 286. If true, the method 260 may continue with the step 280.

A hysteresis assessment 318 may be performed by the step 280, 282, 284, 288, 290, and 292. A check may be performed in the step 280 to see if the isolation method 260 yielded a "true" decision for the last high-speed bin value (HSB). If not, the method 260 may continue with the step 282. If true, the method 260 may continue with the step 284.

In the step 282 a check may be performed to determine if $I_1$ or greater out of the last L values of $H_{HS}$ are marked as high, and the last $J_1$ values of $H_{HS}$ are marked as high. If true, the high-speed bin value (HSB) may be marked true in the step 288. If false, the high-speed bin value (HSB) may be marked false in the step 290.

In the step 284, a check may be performed to determine if $I_2$ or greater out of the last L values of $H_{HS}$ are marked as low, and the last $J_2$ values of $H_{HS}$ are marked as low. If false, the high-speed bin value HSB may be marked true in the step 292. If true, the high-speed bin value HSB may be marked false in the step 290. A high-speed value $H_{HS}$ reaching the step 286 directly from the step 270 may not be considered true or false and the high-speed bin value HSB is marked Not Available. The high-speed bin value (HSB) from the hysteresis assessment 318 may be used to update a high-speed bin output buffer in the step 294. The method 260 may subsequently continue with the step 312.

Returning to the step 262, if the transfer function magnitude |H| is a low-speed value $H_{LS}$ the individual low-speed values $H_{LS}$ may be individually assessed in assessment 317 in the steps 272, 274, and 276. An individual low-speed value $H_{LS}$ may be compared to a low-speed threshold (e.g., $LS_{th}$) in the step 272. If the low-speed value $H_{LS}$ is less than or equal to the low-speed threshold $LS_{th}$, the low-speed value $H_{LS}$ may be marked as a low value in the step 274. If the low-speed value $H_{LS}$ is greater than the low-speed threshold $LS_{th}$, the low-speed value $H_{LS}$ may be marked as a high value in the step 276.

In the step 278, a check may be made to determine if L of the $H_{LS}$ data items have filled the low-speed bin array. If not, the method 260 may continue with step 308. If true, the method 260 may continue with the step 296.

A hysteresis assessment 319 may be performed by the step 296, 298, 300, 302, 304, and 306. A check may be performed in the step 296 to see if the isolation method 260 yielded a "true" decision for the last low-speed bin value (LSB). If not, the method 260 may continue with the step 298. If true, the method 260 may continue with the step 300.

In the step 298 a check may be performed to determine if $I_1$ or greater out of the last L values of $H_{LS}$ are marked as high, and the last $J_1$ values of $H_{LS}$ are marked as high. If true, the low-speed bin value (LSB) may be marked true in the step 302. If false, the low-speed bin value (LSB) may be marked false in the step 304.

In the step 300, a check may be performed to determine if $I_2$ or greater out of the last L values of $H_{LS}$ are marked as low, and the last $J_2$ values of $H_{LS}$ are marked as low. If false, the low-speed bin value LSB may be marked true in the step 306. If true, the low-speed bin value LSB may be marked false in the step 304. A low-speed value $H_{LS}$ reaching the step 308 directly from the step 278 may not be considered true or false and the low-speed bin value LSB is marked Not Available. The low-speed bin value (LSB) from the hysteresis assessment 318 may be used to update a low-speed bin output buffer in the step 310. The method 260 may subsequently continue with the step 312.

In the step 312, a final decision may be made using an isolation truth table. An example isolation truth table is provided as follows:

| Isolation Truth Table | | |
| --- | --- | --- |
| LSB | HSB | Final Decision |
| True | True | True |
| True | False | True |
| True | Not Available | True |
| False | True | True |
| False | False | False |
| False | Not Available | Not Available |
| Not Available | True | True |
| Not Available | False | Not Available |
| Not Available | Not Available | Not Available |

When the final decision is determined by the isolation truth table, a report may be generated by the analyzer 104 in step 314. The method 260 may subsequently return to step 210 in FIG. 9.

The vibration monitoring system 100 may detect internal vibrations at a corner(s) of the vehicle 90 using a single wheel encoder signal for both the input forcing signal and the output response signal to effectively isolate and classify the source of the vibrations. A multiple-input multiple-output analysis or several multiple-input single-output analyses may be performed to isolate and classify the source of the vibrations. An ordinary coherence threshold may be used to determine data sufficiency to perform classification and isolation. Piecewise (in time) matrix operations enable a recursive computationally efficient implementation on embedded microcontrollers. Vibration diagnostics for tire/wheel assemblies may be performed using on-board sensors rather than removing the assemblies for off-vehicle testing. Furthermore, the vibration monitoring system 100 may reduce recurrent visits by customers due to accurate diagnosis.

While the best modes for carrying out the disclosure have been described in detail, those familiar with the art to which this disclosure relates will recognize various alternative designs and embodiments for practicing the disclosure within the scope of the appended claims.

What is claimed is:

1. A vibration monitoring system comprising:
a plurality of encoders configured to generate a plurality of pulse train signals for a plurality of wheels, wherein each of the plurality of encoders is coupled to a respective one of the plurality of wheels and generates a single one of the plurality of pulse train signals; and
an analyzer coupled to the plurality of encoders and configured to
generate both a plurality of pulse per revolution signals and a plurality of angular velocity signals for the plurality of wheels in response to the plurality of pulse train signals, wherein each of the plurality of pulse per revolution signals conveys a single pulse per rotation of the respective wheel,
generate an input phasor array as an n×p array that organizes a plurality of input phasor quantities of the plurality of pulse per revolution signals caused by the plurality of wheels, wherein n represents a plurality of extracted points from each of the plurality of pulse per revolution signals, and p represents the plurality of wheels,
generate a response phasor array as an m×p array that organizes a plurality of response phasor quantities of the plurality of angular velocity signals caused by the plurality of wheels, wherein m represents a plurality of extracted points from the plurality of angular velocity signals, and generate a report that identifies at least one vibrating wheel of the plurality of wheels in response to the input phasor array and the response phasor array.

2. The vibration monitoring system according to claim 1, wherein the analyzer is further configured to re-initialize in response to a change in a physical condition, the change including at least one or more of a change of tire condition, a tire rotation, a tire replacement, a tire repair, a tire pressure monitoring system sensor replacement, and a fault condition in a corresponding one of the plurality of encoders on at least one of the plurality of wheels.

3. The vibration monitoring system according to claim 1, wherein the analyzer is further configured with a set of enabling conditions to ensure robust decision making including at least one or more of a tire pressure within a pressure threshold, friction brakes not engaged, a traction control not active, an acceleration within an acceleration threshold, transitional changes due to manufacturing not present, a servicing not present, a prolonged parking not present, and a sensor validity.

4. The vibration monitoring system according to claim 1, wherein the analyzer is further configured to generate a plurality of matrices for a multiple-input single-output analysis using the input phasor array and the response phasor array.

5. The vibration monitoring system according to claim 4, wherein the analyzer is further configured to group a plurality of entries of the plurality of matrices into a plurality of low-speed bins and a plurality of high-speed bins.

6. The vibration monitoring system according to claim 5, wherein the analyzer is further configured to check a plurality of ordinary coherence factors of the plurality of matrices in the plurality of low-speed bins and the plurality of high-speed bins to confirm data sufficiency to perform classification and isolation.

7. The vibration monitoring system according to claim 6, wherein the analyzer is further configured to generate a plurality of transfer function values in response to the plurality of matrices, and generate a plurality of multiple coherence values in response to the plurality of transfer function values and the plurality of matrices to confirm linearity of the transfer function values.

8. The vibration monitoring system according to claim 7, wherein the analyzer is further configured to identify the at least one vibrating wheel in response to the plurality of transfer function values in the plurality of low-speed bins and the plurality of high-speed bins.

9. The vibration monitoring system according to claim 8, wherein the identifying of the at least one vibrating wheel is in response to one or more of historical statistics and an isolation truth table.

10. A method for wheel vibrational monitoring comprising:
generating a plurality of pulse train signals for a plurality of wheels with a plurality of encoders, wherein each of the plurality of encoders is coupled to a respective one of the plurality of wheels and generates a single one of the plurality of pulse train signals;
generating both a plurality of pulse per revolution signals and a plurality of angular velocity signals for the plurality of wheels in response to the plurality of pulse train signals with an analyzer, wherein each of the plurality of pulse per revolution signals conveys a single pulse per rotation of the respective wheel;
generating an input phasor array as an n×p array that organizes a plurality of input phasor quantities of the plurality of pulse per revolution signals caused by the plurality of wheels, wherein n represents a plurality of extracted points from each of the plurality of pulse per revolution signals, and p represents the plurality of wheels;
generating a response phasor array as an m×p array that organizes a plurality of response phasor quantities of the plurality of angular velocity signals caused by the plurality of wheels, wherein m represents a plurality of extracted points from the plurality of angular velocity signals; and
generating a report that identifies at least one vibrating wheel of the plurality of wheels in response to the input phasor array and the response phasor array.

11. The method according to claim 10, further comprising re-initializing the analyzer in response to a change in a physical condition, the change including at least one or more of a change of tire condition, a tire rotation, a tire replacement, a tire repair, a tire pressure monitoring system sensor replacement, and a fault condition in a corresponding one of the plurality of encoders on at least one of the plurality of wheels.

12. The method according to claim 10, wherein a set of enabling conditions to ensure robust decision making in the analyzer includes a tire pressure within a pressure threshold, friction brakes not engaged, a traction control not active, an acceleration within an acceleration threshold, transitional changes due to manufacturing not present, a servicing not present, a prolonged parking not present, and a sensor validity.

13. The method according to claim 10, further comprising generating a plurality of matrices for a multiple-input single-output analysis using the input phasor array and the response phasor array.

14. The method according to claim 13, further comprising grouping a plurality of entries of the plurality of matrices into a plurality of low-speed bins and a plurality of high-speed bins.

15. The method according to claim 14, further comprising checking a plurality of ordinary coherence factors of the plurality of matrices in the plurality of low-speed bins and the plurality of high-speed bins to confirm data sufficiency to perform classification and isolation.

16. The method according to claim 15, further comprising:
generating a plurality of transfer function values in response to the plurality of matrices; and
generating a plurality of multiple coherence values in response to the plurality of transfer function values and the plurality of matrices to confirm linearity of the transfer function values.

17. The method according to claim 16, further comprising identifying the at least one vibrating wheel in response to the plurality of transfer function values in the plurality of low-speed bins and the plurality of high-speed bins.

18. The method according to claim 17, wherein the identifying of the at least one vibrating wheel is in response to one or more of historical statistics and an isolation truth table.

19. The method according to claim 10, the plurality of wheels support a moving vehicle.

20. A vehicle comprising:
a plurality of wheels configured to support the vehicle;
a plurality of encoders configured to generate a plurality of pulse train signals for the plurality of wheels, wherein each of the plurality of encoders is coupled to a respective one of the plurality of wheels and generates a single one of the plurality of pulse train signals; and an analyzer coupled to the plurality of encoders and configured to
generate both a plurality of pulse per revolution signals and a plurality of angular velocity signals for the plurality of wheels in response to the plurality of pulse train signals, wherein each of the plurality of pulse per revolution signals conveys a single pulse per rotation of the respective wheel,
generate an input phasor array as an n×p array that organizes a plurality of input phasor quantities of the plurality of pulse per revolution signals caused by the plurality of wheels, wherein n represents a plurality of extracted points from each of the plurality of pulse per revolution signals, and p represents the plurality of wheels,
generate a response phasor array as an m×p array that organizes a plurality of response phasor of the plurality of angular velocity signals caused by the plurality of wheels, wherein m represents a plurality of extracted points from the plurality of angular velocity signals, and
generate a report that identifies at least one vibrating wheel of the plurality of wheels in response to the input phasor array and the response phasor array.

* * * * *